United States Patent [19]
Mathewson et al.

[11] Patent Number: 5,236,665
[45] Date of Patent: Aug. 17, 1993

[54] HOLLOW FIBER TREATMENT APPARATUS AND MEMBRANE OXYGENATOR

[75] Inventors: Wilfred F. Mathewson, Bonsall; Philip L. Ritger, Huntington Beach, both of Calif.

[73] Assignee: Baxter International Inc., Deerfield, Ill.

[21] Appl. No.: 971,717

[22] Filed: Nov. 4, 1992

Related U.S. Application Data

[63] Continuation of Ser. No. 516,960, Apr. 30, 1990, abandoned, which is a continuation-in-part of Ser. No. 260,164, Oct. 20, 1988, Pat. No. 5,120,501.

[51] Int. Cl.$^5$ .............................. A61M 1/14
[52] U.S. Cl. ....................... 422/46; 422/48; 128/DIG. 3; 261/DIG. 28; 210/321.81; 210/321.9; 210/492; 210/496; 210/499; 210/500.23; 95/46; 96/6
[58] Field of Search ............... 422/46, 48; 55/16, 158; 128/DIG. 3; 261/DIG. 28; 210/321.81, 321.9, 492, 496, 499, 500.23, 500.36

[56] References Cited

U.S. PATENT DOCUMENTS

| | | | |
|---|---|---|---|
| 3,536,611 | 10/1970 | de Filippi et al. | 210/321.89 |
| 3,557,296 | 1/1971 | Kohl | 210/321 |
| 3,557,962 | 1/1971 | Kohl | 210/321 |
| 3,794,468 | 2/1974 | Leonard | 210/321.79 |
| 3,893,926 | 7/1975 | Awad | 422/48 X |
| 3,957,648 | 5/1976 | Roget et al. | 210/494 |
| 3,963,622 | 6/1976 | Baudet et al. | 210/321 |
| 3,998,593 | 12/1976 | Yoshida | 422/48 X |
| 4,020,230 | 4/1977 | Mahoney et al. | 428/398 |
| 4,140,637 | 2/1979 | Walter | 210/321.9 |
| 4,172,794 | 10/1979 | Sigdell | 210/232 |
| 4,246,120 | 1/1981 | Baudet et al. | 55/158 X |
| 4,261,951 | 4/1981 | Miley | 422/46 |
| 4,272,373 | 6/1981 | Stenberg et al. | 422/48 X |
| 4,293,418 | 10/1981 | Fujii et al. | 55/158 X |
| 4,306,018 | 12/1981 | Kirkpatrick | 435/2 |

(List continued on next page.)

FOREIGN PATENT DOCUMENTS

| | | |
|---|---|---|
| 0089122 | 2/1983 | European Pat. Off. |
| 0176651 | 2/1984 | European Pat. Off. |
| 0285812 | 3/1988 | European Pat. Off. |
| 0345983 | 5/1989 | European Pat. Off. |
| 2839937 | 9/1978 | Fed. Rep. of Germany |
| 286426 | 12/1986 | Japan |
| WO90/04419 | 5/1990 | PCT Int'l Appl. |

Primary Examiner—Lynn M. Kummert
Attorney, Agent, or Firm—Raymond Sun; Michael C. Schiffer

[57] ABSTRACT

A hollow fiber membrane fluid treatment apparatus for the transfer of mass or energy through the membrane is disclosed. It is designed particularly, but not only, for use in membrane oxygenators. Hollow fiber membranes extend substantially longitudinally, first inert fibers are spaced between them and also extend substantially longitudinally. Second inert fibers extend generally transverse to the hollow fibers and generally contiguous therewith, so that a first fluid (preferably an oxygen-containing gas) can pass through the hollow fibers and a second fluid (preferably blood) can be passed over their exterior for mass or energy transfer through the membrane. Usually the second inert fibers form a weft and the first inert fibers are spaced one between each two hollow fibers so that the warp consists of alternating strands of hollow fiber and first inert fiber passing over the weft in an oscillating fashion to define at least in part the size of the fluid film to be passed over the hollow fiber membrane for mass or energy transfer through the membrane. The inert fibers are usually biocompatible monofilament polymers which provide precise spacing of the hollow fibers to produce even blood films. Usually, the apparatus is disposed in a blood passageway of a membrane oxygenator, and layered in ribbons sized to fit the blood channel with the first inert fibers spacing the hollow fibers so that the hollow fibers are offset with respect to each other from layer to layer.

32 Claims, 9 Drawing Sheets

U.S. PATENT DOCUMENTS

| | | | |
|---|---|---|---|
| 4,346,006 | 8/1982 | Kopp et al. | 210/321.4 |
| 4,368,124 | 1/1983 | Brumfield | 210/321.3 |
| 4,374,802 | 2/1983 | Fukusawa | 422/48 |
| 4,376,095 | 3/1983 | Hasegawa | 422/46 |
| 4,424,190 | 1/1984 | Mather, III et al. | 422/46 |
| 4,428,403 | 1/1984 | Lee et al. | 138/130 |
| 4,499,842 | 2/1985 | Mahr | 114/103 |
| 4,572,446 | 2/1986 | Leonard et al. | 242/7.02 |
| 4,620,965 | 11/1986 | Fukusawa et al. | 422/46 |
| 4,622,206 | 11/1986 | Torgeson | 422/48 |
| 4,639,353 | 1/1987 | Takemura et al. | 422/46 |
| 4,645,645 | 2/1987 | Martinez et al. | 422/46 |
| 4,657,743 | 4/1987 | Kanno | 422/46 |
| 4,659,549 | 4/1987 | Hamada et al. | 422/48 |
| 4,698,207 | 10/1987 | Bringham et al. | 422/46 |
| 4,715,953 | 12/1987 | Leonard | 210/321.8 |
| 4,808,378 | 2/1989 | Nakanishi et al. | 422/48 |

HOLLOW FIBER TREATMENT APPARATUS AND MEMBRANE OXYGENATOR

This is a continuation of application Ser. No. 07/516,960 filed on Apr. 30, 1990, now abandoned, which is continuation-in-part of U.S. application Ser. No. 260,164, filed Oct. 20, 1988, now U.S. Pat. No. 5,120,501 for integrated Membrane Oxygenator/Heat Exchanger, which is incorporated herein as though fully set forth.

BACKGROUND OF THE INVENTION

This invention relates to hollow fiber fluid treatment devices, particularly such devices used for mass or energy exchange through the membrane, i.e. heat exchangers, dialyzers, and in particular membrane oxygenators for the oxygenation of blood in cardiopulmonary bypass blood circuits. Membrane oxygenators direct blood passing through an extracorporeal circuit into contact with a surface or membrane, usually a hollow fiber membrane, through which gas can diffuse or be transferred. The surfaces or membranes are used to transfer oxygen and carbon dioxide between the blood and an oxygen-bearing gas.

Hollow fiber fluid treatment devices have been developed for uses other than oxygenation and some are shown in the following U.S. Pat. Nos.: 3,536,611 to DeFilippi et al., 3,557,962 to Kohl, 3,794,468 to Leonard, 3,957,648 to Roget et al., 4,020,230 to Mahoney, 4,140,637 to Walter, 4,172,794 to Sigdell, and 4,368,124 to Brumfield.

Turning to fluid treatment apparatus for oxygenators, U.S. Pat. No. 4,374,802 to Fukusawa, U.S. Pat. No. 4,376,095 to Hasegawa, 4,657,743 to Kanno, and 4,698,207 to Bringham et al. generally disclose an oxygenator with lengthwise-extending hollow fibers which contain the blood; gas is passed over the fibers. U.S. Pat. Nos. 4,620,965 to Fusakawa, 4,659,549 to Hamada, and EPO published application 0.176.671 generally disclose an oxygenator with similar longitudinally extending fibers containing the oxygen-rich gas; blood flows over the fibers. Another disclosure along this line is found in U.S. Pat. No. 4,645,645 to Martinez, et al. Yoshida, U.S. Pat. No. 3,998,593 discloses a membrane oxygenator having alternate layers of rectangular polymer membranes and rectangular mesh spacers forming alternate gas channels and blood channels.

Other oxygenators have been developed disclosing helically wound fibers, for example, U.S. Pat. No. 4,306,018 to Kirkpatrick, U.S. Pat. No. 4,715,953 to Leonard, Japanese Laid Open Patent Application Ser. No. 286426/86 to Japan Medical Supply Co., Ltd.. U.S. Pat. No. 4,424,190 to Mather III, Bringham et al., mentioned above, and U.S. Pat. No. 4,808,378 to Nakanishi. An invention directed to a method of winding a bundle of hollow fibers around a core for an oxygenator is disclosed in U.S. Pat. No. 4,572,446 to Leonard.

Blood is passed through a tubular membrane containing a group of capillary membranes extending spirally through it in U.S. Pat. No. 3,893,926, to Awad, and a somewhat similar arrangement is said to be applicable to oxygenators in U.S. Pat. Nos. 3,963,622 and 4,246,120 to Baudet, et al.

A diffusion membrane unit said to be applicable to oxygenators is disclosed in U.S. Pat. No. 4,346,006 to Kopp, et al. The unit includes a plurality of separate, parallel membrane tubes formed into a flat, substantially two-dimensional array joined by adhesive in spaced relation to each other for improved exposure of the exterior of the tubular membrane to the passing fluid. The adhesive may be a material similar to the membrane material and extends continuously across the parallel membrane tubes. In another embodiment, the unit contains a plurality of planar, single-layered arrays of parallel capillary tubes defining out of phase sinuous paths.

A device for the extracorporeal treatment of blood is disclosed in U.S. Pat. No. 4,428,403 to Lee, et al. It consists of hollow tubing with plastic monofilament wrapped around its outer surface in a generally spiral configuration, preferably then formed into a coil in which the coils are spaced apart by the monofilament.

A membrane oxygenator is also disclosed in U.S. Pat. No. 4,622,206 to Torgeson. It has a housing with hollow fibers extending cross-wise, where the blood flows transversely over the fibers. The fibers are placed in a layer at a center to center spacing of about 1.5 to 4 times the diameter of the fibers. Filaments may be positioned between at least some of the fibers to improve spacing and facilitate more efficient transfer. Fibers may be wound around a frame member and adjacent layers preferably have fibers angularly offset with respect to each other.

One primary disadvantage, however, of commercially available membrane oxygenators containing membrane units such as the above pertains to the relatively large "priming volume" of the extracorporeal circuit which includes such devices. The total internal volume of the extracorporeal circuit, which includes the oxygenation and heat exchange devices as well as other devices, is flushed out before surgery to remove any extraneous gas from the extracorporeal circuit. "Priming" is typically performed with a biocompatible solution, e.g. a saline solution, which then mixes with the patient's blood, causing dilution of the blood cells, and in particular the red blood cells for a given volume of fluid. To minimize such hemodilution, donor blood may have to be introduced into the diluted blood passing through the extracorporeal circuit.

While the addition of donor blood ma)k reduce hemodilution, it presents other complications, such as compatibility problems between the donor blood and patient's blood and complications associated with blood-borne diseases. As a result, other measures can be taken to correct the effects of hemodilution, such as using hemoconcentrators to concentrate the blood cell count. However, they are expensive and cumbersome to operate, and may injure the blood cells.

It is thus apparent that it would be advantageous to design a very efficient hollow fiber membrane apparatus in order to reduce the priming volume of the oxygenator. The major impediment to doing so, however, is the requirement of providing sufficient surface area for both heat exchange and for oxygenation. As to oxygenation, this requires a well-designed hollow fiber fluid treatment apparatus within the oxygenator to obtain sufficient oxygen transfer rates.

Another problem which may occur with membrane oxygenators is injury to or deterioration of the blood as it passes through or over the hollow fiber membranes. Stagnant areas result in thrombogenicity, while rapid flow rates in some areas result in shear stresses which cause hemolysis. Thus, it is desirable to produce a hollow fiber system with as uniform and even blood flow as possible, in order to minimize blood injury.

SUMMARY OF THE INVENTION

The present invention overcomes the above-mentioned problems and disadvantages of hollow fiber fluid treatment devices and membrane oxygenators which utilize them. In the present invention, in one aspect, the membrane arrangement is designed to provide a very high membrane surface area for fluid contact in a minimum volume, with thin, uniform fluid flow throughout.

For the purpose of the present invention, the term "gas permeable membrane", "hollow fiber", or "hollow fiber membrane" is meant to include any substrate formed from the material which functions to allow for the transfer or diffusion of gas from one side of the substrate to the other and, in the particular application, a substrate formed from a material which allows for transfer or diffusion of oxygen and carbon dioxide gas.

In one aspect, the invention is a hollow fiber membrane fluid treatment apparatus for the transfer of mass or energy through the membrane which includes hollow fiber membranes extending substantially longitudinally, first inert fibers spaced between said hollow fibers and also extending substantially longitudinally, and second inert fibers extending generally transverse to the hollow fibers and generally contiguous therewith, so that a first fluid can pass through the hollow fibers and a second fluid can be passed over their exterior for mass or energy transfer through the membrane. Preferably, the hollow fibers and first inert fibers comprise a warp and the second inert fibers comprise a weft to form a hollow fiber membrane weave.

Usually the hollow fibers extend through the weave aligned straight relative to the first inert fibers, which follow an oscillating path about the second inert fibers. The first inert fibers are spaced so that the warp consists of alternate strands of hollow fiber and first inert fiber and the size of the first inert fibers defines (at least in part) the size of the fluid film to be passed over the hollow fiber membrane for mass or energy transfer through the membrane. For use in an oxygenator, biocompatible materials are used, preferably microporous polypropylene for the hollow fibers and monofilament polymers for the inert fibers because the spacing between the hollow fibers can thus be closely controlled. Most preferably, the monofilaments are polyester.

In another aspect, the invention is a membrane oxygenator containing such a hollow fiber weave for oxygenation of (and removal of carbon dioxide from) the blood. In this aspect, the oxygenator consists of apparatus having a blood inlet and outlet and a gas inlet and outlet and also having at least one channel with a base which forms a primary conduit for a second fluid, where the channel contains the hollow fiber weave described above with the hollow fibers extending substantially lengthwise through the channel to form a conduit, preferably for the oxygen-containing gas.

Preferably, the first inert fibers are each about one fifth to one third the diameter of the hollow fibers and the second inert fibers are each about one eighth to one fifth the diameter of the hollow fibers and spaced about five to the inch to promote the flow of thin films of blood and high oxygen transfer rates. Generally, the hollow fibers are disposed in the channel in woven ribbons sized to fit the channel and arranged in alternating layers, the first inert fibers in alternate layers being about one third the diameter of the hollow fibers, and the first inert fibers in the remaining layers being about one fifth the diameter of the hollow fibers so that the hollow fibers in adjacent layers are generally offset from each other to promote even spacing between the layers and even blood flow throughout. In other aspects, the first inert fibers alternate in size in each ribbon so that the ribbons can be layered with the hollow fiber membranes of each layer offset from those of adjacent layers.

In the preferred membrane oxygenator, the woven ribbons are disposed in the channel spaced from the base with a spacer to define a gap adjacent the base. The gap forms a first channel for blood passage, where the bulk of the heat exchange occurs, the second channel for blood passage, directed primarily to oxygenation, being through the ribbons. Preferably, the hollow fibers are disposed in the channel in about thirty-two woven ribbons having either about 6 or about 7 hollow fibers each, and a coiled spacer extends the length of the channel in the gap to maintain the integrity of the gap and the position of the ribbons during manufacture and use of the oxygenator.

In a preferred aspect, the invention includes a blood oxygenator and heat exchange device containing a housing defining a first internal chamber, and a first thermally conductive core positioned inside the housing internal chamber, the core being formed with an internal region through which a heat exchange fluid can be directed and a first external surface with a plurality of separate, adjacently positioned parallel blood receiving channels. A hollow fiber membrane fluid treatment apparatus described above is arranged in each of the channels, each hollow fiber membrane defining a separate gas flow pathway which is open at opposite ends of said membranes. A gas manifold associated with the housing has two gas channels, each gas channel communicating with ends of the hollow fiber membranes and ports through which gas can be introduced or removed. A blood manifold means is mounted in the housing and adjacent to the core for delivering blood to the blood receiving channels.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

The present invention is directed to a hollow fiber membrane fluid treatment apparatus for the transfer of material (or energy in the case of a heat exchange device) between one fluid and another. In the preferred embodiment, it is a hollow fiber weave for the oxygenation of blood in a membrane oxygenator, and an oxygenator containing such a hollow fiber fluid treatment apparatus.

Figure 9:
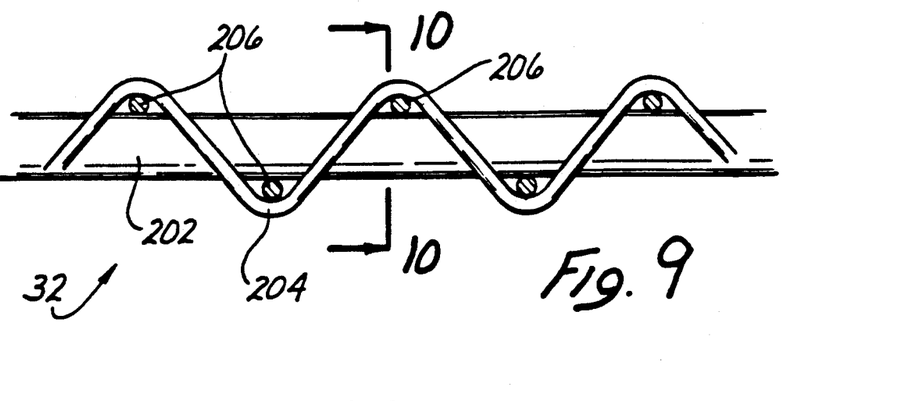
FIG. 9 is a side elevation of the preferred hollow fiber weave of the present invention.
Figure 10:
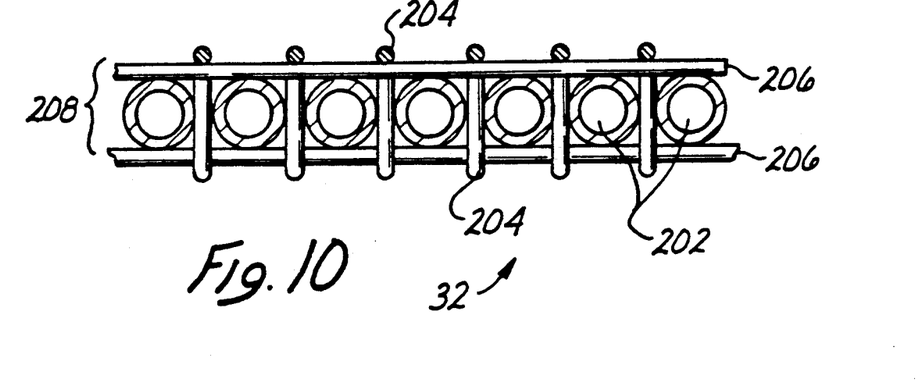
FIG. 10 is a cross-section of the hollow fiber weave of the present invention taken at lines 10—10 of FIG. 9.

Referring first to FIGS. 9 and 10, the preferred hollow fiber fluid treatment apparatus can be seen. The fluid treatment device includes a bundle 32 of hollow fiber membranes 202. The hollow fibers 202 extend generally parallel to each other in a substantially longitudinal direction and are spaced between first inert fibers 204, preferably monofilaments, also extending substantially longitudinally. In the preferred embodiment, fibers 202 and 204 form the warp of what amounts to a hollow fiber weave or, most preferably, woven ribbon 208. Second inert fibers 206 are also included; they usually extend transverse and contiguous to the hollow fibers 202, preferably spaced alternately above and below fibers 202 to form the weft of weave or ribbon 208. The first inert fibers 204, preferably flexible relative to the hollow fibers 202, pass above and below the second inert, or weft, fibers 206 in a sinuous or oscillating path.

In the preferred fluid treatment apparatus of the present invention, the hollow fibers form a conduit for oxygen gas, oxygen-rich gas, or oxygen-containing gas, (all hereafter referred to as "oxygen-containing gas") to oxygenate the blood, which passes over the surface of the fibers. In addition, carbon dioxide is removed from the blood through the membrane. Useful membrane materials for the hollow fiber membranes may be silicone, polyolefins such as polypropylene or polyethylene or another suitable hydrophobic polymeric material. These types of membranes will allow oxygen to pass from an oxygen-bearing gas to the blood, which is oxygen deficient, while allowing for the transfer of carbon dioxide from the blood to the gas. In general, the porosity of the membrane is selected according to the requirements of the invention, and in the present case, the membrane selected should be biocompatible and allow for the selective diffusion of oxygen and carbon dioxide while inhibiting the passage of liquids.

The types of hollow fiber membranes useful for the practice of the invention are well known, with such membranes described in any one of the above mentioned U.S. patents issued to Mather III et al, Kanno. Hasegawa and Leonard. All such relevant disclosures to such membranes are incorporated herein by reference. As is well known, however, the rate of gas exchange is dependent upon the permeability of the membrane, as well as the partial pressure of the gases being exchanged within the associated fluid, that is, the oxygen-bearing gas and the blood. For a more detailed description of such membranes, and theory of operation, see "Cardiopulmonary Bypass", 2nd Edition, Charles C Reed and Trudi B. Stafford, Texas Medical Press, Inc, 1985, Chapter 28 "Membrane Oxygenator", pages 427–449, which description with respect to such membranes is incorporated herein by reference.

The preferred material for the hollow fiber membrane of the present invention is microporous polypropylene, in particular Oxyphan ® membrane, Oxyphan ® being a registered trademark of ENKA AG. Oxyphan ® is a hydrophobic microporous polypropylene membrane made by a thermally induced phase separation process.

The preferred form of Oxyphan ® is Oxyphan ® 50/280, meaning that the internal diameter of the hollow fibers is about 280 microns while the wall thickness is about 50 microns. However, for a blood oxygen transfer application such as the present one, the internal diameter range for the hollow fibers will generally be about 100–500 microns, preferably 200–400 microns and optimally about 280 microns, while the wall thickness range will be about 30–80 microns, preferably about 35–60 microns and preferably about 50 microns. In the case of the wall thickness, a trade off is made between gas pressure within the fiber and stability of the structure; below about 30 microns in wall thickness, the hollow fibers may become too fragile for easily handling. The void volume is preferably about fifty (50) percent.

Turning to the first inert fibers 204 (which form part of the warp of ribbon 208), they are preferably flexible relative to the hollow fiber membrane itself and formed of a biocompatible material such as polyester, nylon or polypropylene; the preferred polymer is polyester and the preferred first inert fibers 204 are made of polyester monofilament. Different materials, of course, can be used for the first inert fibers 204 but, in general, these materials, if used in an oxygenator, must be biocompatible, strong, and easy to handle. The use of monofilament for the first inert fibers is very useful in an oxygenator such as the present one because it can be obtained at very close tolerances, and can be used to define a ribbon 208 with very precise spacing between the hollow fibers, to optimize the uniformity of the film of blood flowing over the hollow fibers for optimum gas exchange and minimum blood injury.

In the present case, first inert fibers 204 are preferably about 1/10 to ½ the diameter of the hollow fiber membrane, more preferably 1/5 to ⅓ the diameter of the hollow fiber membrane 202. This precise sizing of monofilament 204, plus the generally sinusoidal or oscillating arrangement of the monofilament 204 relative to the hollow fiber membrane 202, allows passage of the blood through the weave 208 immediately adjacent to and over the hollow membranes 202 in extremely thin films defined at least in part by the size of the fibers 204. Blood films so thin are unusual and provide very effective oxygenation. In the preferred embodiment, the first inert fibers in each ribbon 208 are either one-fifth or one-third the diameter of the hollow fibers; in alternate embodiments, they may alternate within a single ribbon 208 to vary the spacing between the hollow fibers.

The second inert fibers 206, the weft fibers, can be formed of the same materials and in the preferred embodiment are similarly formed of polyester monofilament. They stabilize the weave and position the first inert monofilament fibers 204 in their oscillating path above and below the plane of the hollow fibers. In general, the membrane fiber 202 is much larger in width than the second inert fibers 206. The weft fibers 206 are positioned preferably every ½ to 1/16 inch along the length of the membranes, most preferably about 1/5 inch apart, and preferably have a diameter 1/20th to 1/5th, most preferably 1/8th, that of the hollow fiber 202.

Figure 1:
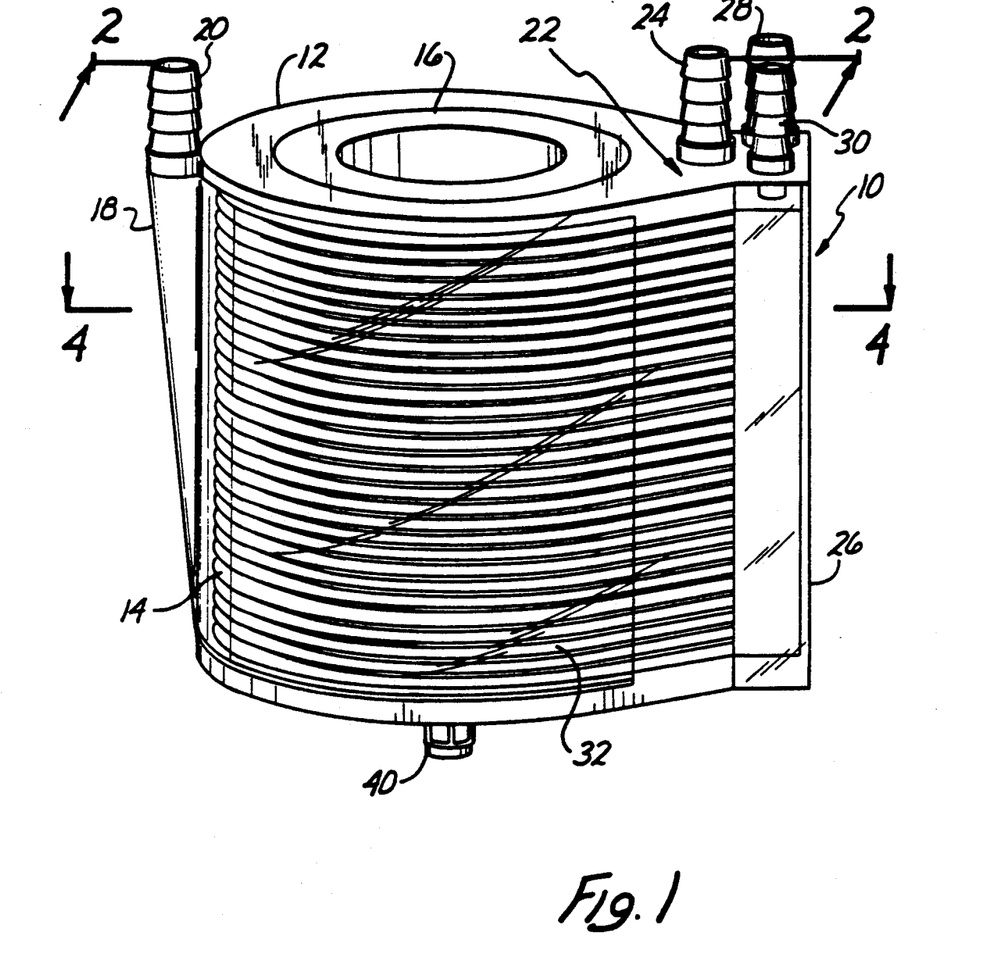
FIG. 1 is a perspective side view of a blood oxygenator/heat exchange device in accordance with an embodiment of the invention.
Figure 12:
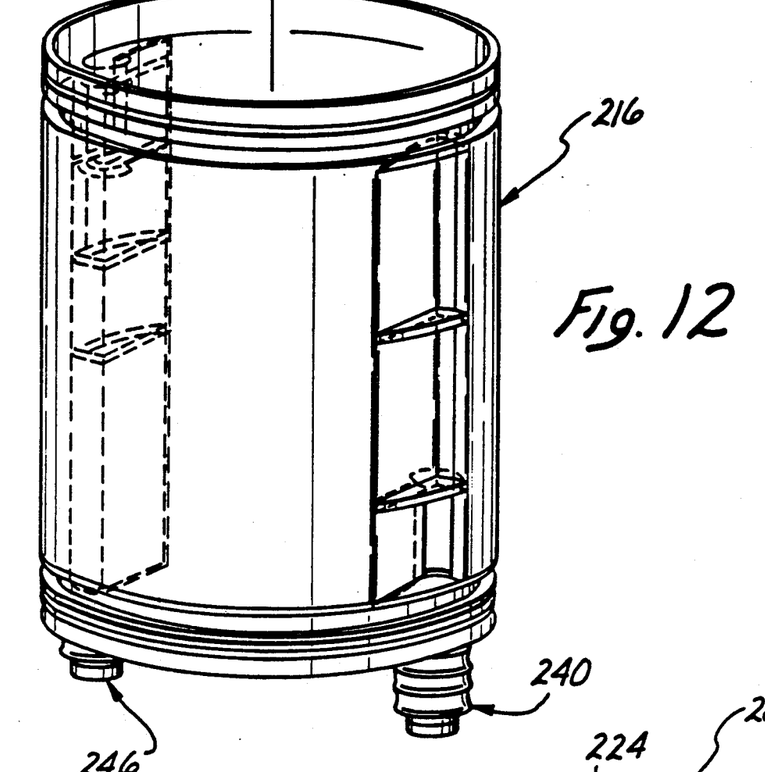
FIG. 12 is a side elevation of the preferred heat exchange jacket for the present oxygenator.

Turning now to FIG. 1, a specific embodiment of the heat exchanger/oxygenator containing the present fluid treatment apparatus will now be described. The heat exchanger/oxygenator is seen generally at 10. It will be connected in an extracorporeal circuit for the purpose of raising or lowering the blood temperature, and performing the necessary gas exchange. The device 10 generally includes an outer housing enclosure 12, in which is mounted a heat exchange body, or bellows 14 and a heat exchange jacket 16. An alternate preferred heat exchange jacket 216 is shown in FIG. 12.

Figure 2:
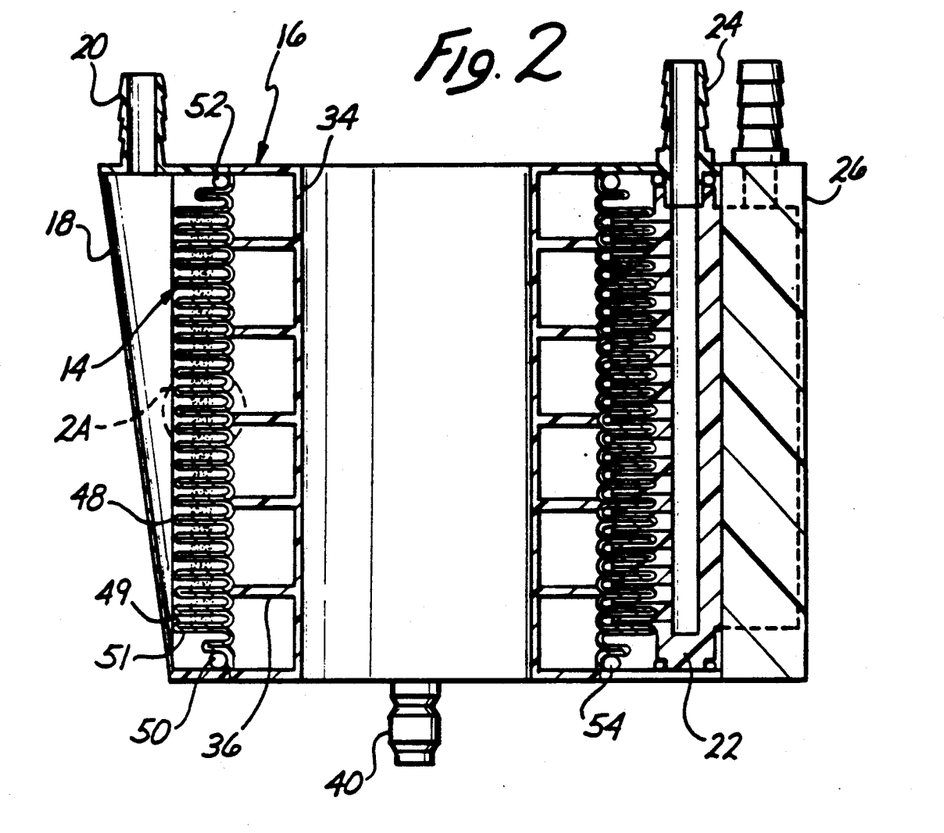
FIG. 2 is a cross-sectional view of FIG. 1 along line 2—2.
Figure 2A:
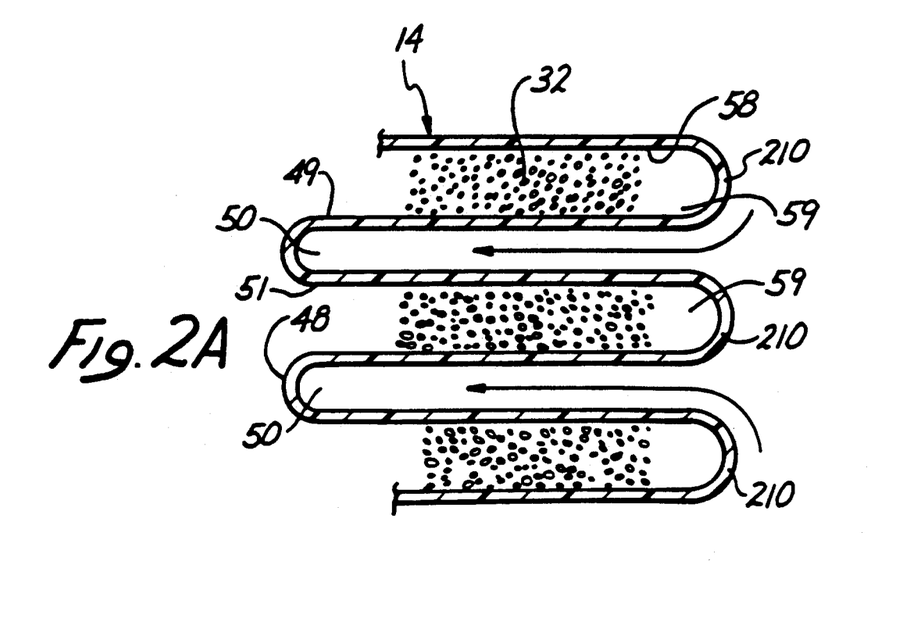
FIG. 2A is an enlarged view of the blood receiving channels, as defined by the pleats of the bellows and the hollow fiber membranes, as seen generally in FIG. 2.
Figure 11A:
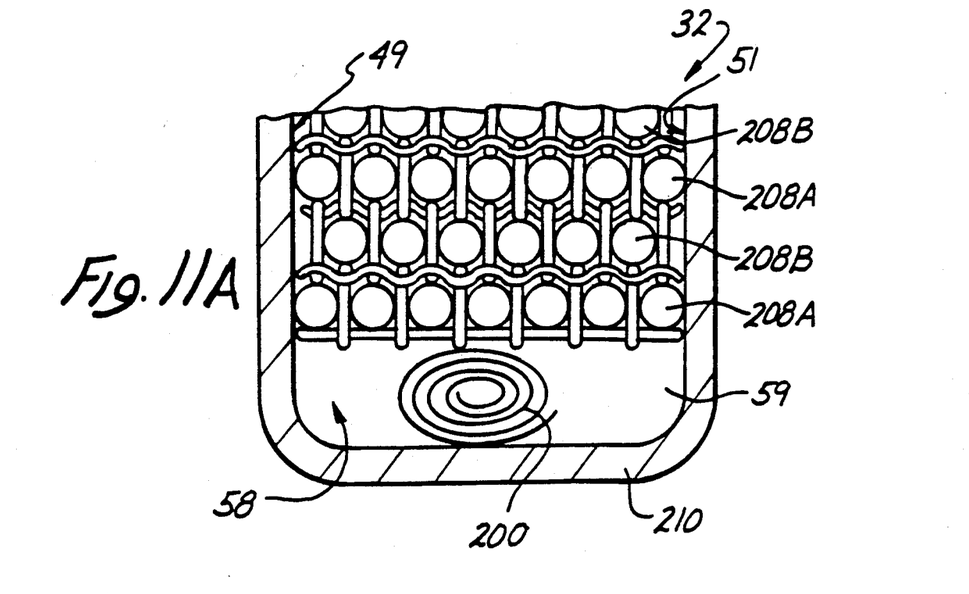
FIG. 11A is a cross-section of a preferred hollow fiber fluid treatment apparatus of the present invention layered in a blood flow channel of an oxygenator.

The bellows 14 is formed with a plurality of pleats 48, the precise number of which is dependent on the desired characteristics of the oxygenator with a blood receiving channel defined between each of the adjacently positioned pleats 48, such channels best seen in FIG. 11 and 2A at 58. The illustrated blood receiving channels 58 are arranged about the circumference of the cylindrically shaped bellows 14 in a substantially parallel orientation. Blood is directed through each of the channels 58 for the purpose of performing the heat exchange and gas exchange.

Each pleat 48 is defined by two walls, seen generally at 49 and 51, which are usually angularly positioned with respect to each other. The inner surface of the walls 49 and 51 define a space 50, which is positioned along the inner side of the bellows 14 opposite channels 58. Space 50 faces jacket 16 to define a portion of fluid pathway 38. Fluid travels through this space 50 and comes into intimate contact with walls 49 and 51. The opposite surfaces of these walls 49 and 51 define the blood receiving channels 58. The blood passing through the blood receiving channels 58 will thus come into intimate contact with the other surfaces of the walls 49 and 51 to ensure efficient cooling or heating of the blood.

The heat exchange jacket 16 or 216, which is positioned within the bellows 14, defines a fluid passage, through which a heat exchange fluid passes to heat or cool the bellows 14. The heat exchange jacket 16 is designed to direct the fluid against the inside surface of the heat exchange body 14, which is formed from a thermally conductive material, i.e. metal. The fluid will thus either heat or cool the body 14, with the blood being directed across the surface of the heat exchange body 14 to effect the necessary heat exchange. Heat exchange jacket 16 directs the fluid through a pathway 37 defined by lips 36, while heat exchange Jacket 216 directs the fluid over its smooth surface from entry 240, the slanted surface 241 and the bellows (to be discussed) channelling the fluid and forming the fluid path 237.

The housing enclosure 12 is also formed with a blood exit manifold 18, and exit tubing connector 20. Blood passing through the device 10 will collect in the exit manifold 18 and exit through the tubing connector 20. A tube, not shown, coupled to the tubing connector 20, will direct the blood back to the patient or to another device in the extracorporeal circuit, not shown. Blood enters the device 10 through a blood manifold, seen generally at 22 (or 222 in FIG. 13) which is fitted into the housing enclosure 12. The blood manifold 22 or 222 is formed to deliver blood to the individual blood receiving channels 58. The manifold 22 or 222 also includes a blood inlet tubing connector 24 to which a suitable tubing, not shown, is coupled for delivering blood to the device 10 from the patient.

The device 10 further includes a gas manifold 26. This gas manifold 26 may either be a separate structure mounted to the device housing enclosure 12, or integrally formed therewith, and is formed to deliver a gas, typically an oxygen-containing gas, i.e. either pure oxygen or blends of oxygen with other suitable gas, e.g. nitrogen, to the gas passage defined by the gas permeable membrane 202.

In accordance with the preferred embodiment as illustrated in FIGS. 9, 10 and 11, hollow fiber membranes 202 are formed in ribbons arranged between adjacently positioned pleats of the bellows 14. These ribbons 208 generally are wrapped about the bellows 14 and the flood manifolds 22 or 222, with the opposing ends of each of the fibers 202 positioned contiguously along the line of the bellows 14 and embedded within a potting polymeric composition, seen at 60. The urethane potting material 60 may be selected from any suitable potting material, e.g., any of the urethane potting materials taught by the above-incorporated references and, in particular the Leonard patent.

As stated, the opposite open ends of the hollow fibers 202 in ribbons 208 forming hollow fiber bundle 32 are embedded within the potting material in a side by side relationship. This forms rows of the ends of ribbons 208, with such rows seen in FIG. 4 at 31 and 33. The respective individual fiber ends are exposed at a surface of the potting material to provide access into the fibers. Typically, after the fibers have been potted a layer of the potting material, in which the fibers are embedded, is removed to expose the open ends of the individual fibers.

Figure 3:
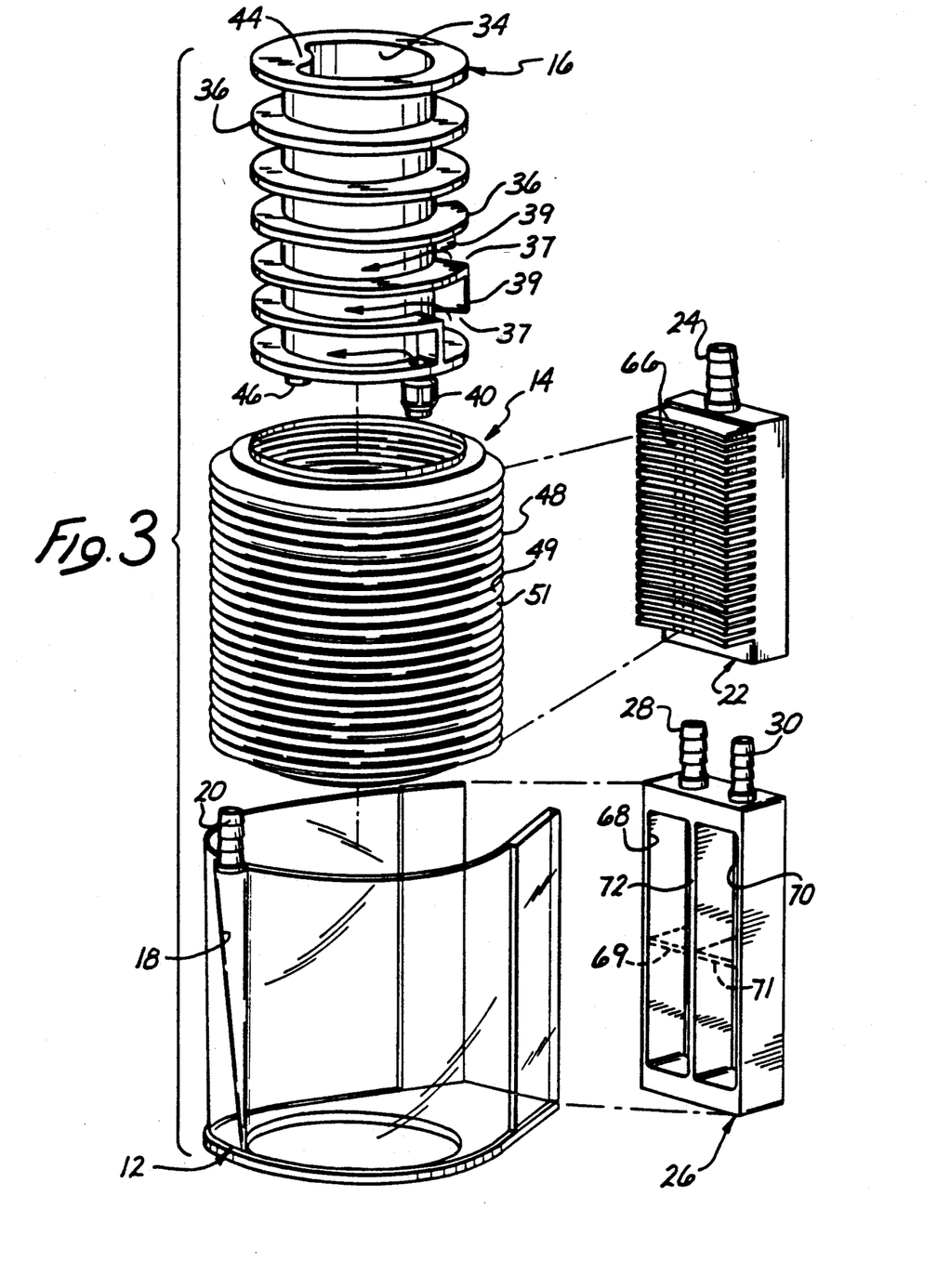
FIG. 3 is an exploded view of the device of FIG. 1.
Figure 4:
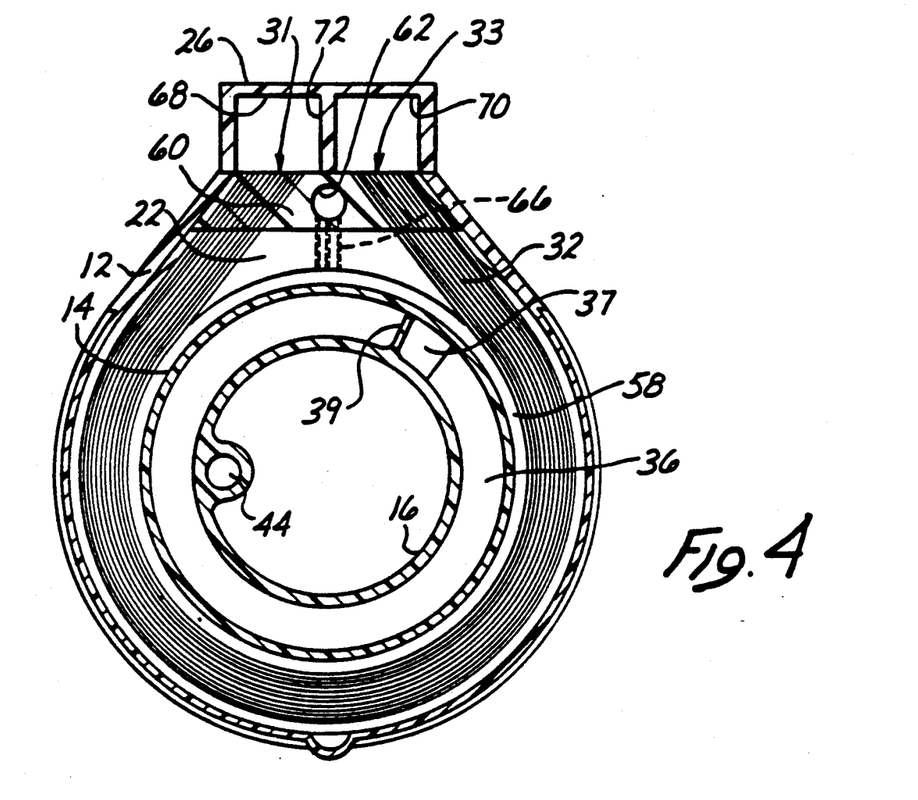
FIG. 4 is a cross-sectional view of FIG. 1 along line 4—4.
Figure 13:
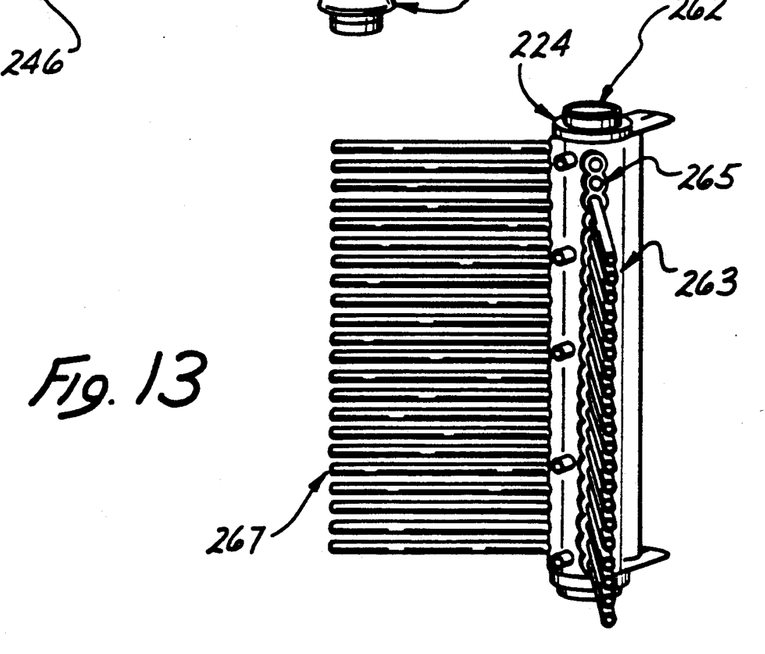
FIG. 13 is a side elevation of the preferred blood manifold of the oxygenator of the present invention.

The urethane potting material 60, not only fixes the fibers 202 in position, but also fixes the blood manifold 22 or 222 in the housing 12. One blood manifold 22, is best seen in FIG. 3, is an elongated body formed with a centrally disposed conduit 62 running through its length, as seen in FIG. 4. This conduit 62 is closed at one end and open at the opposite end to the blood inlet tubing connector 24. The preferred cylindrical blood manifold 222 is shown in FIG. 13, also having a conduit 262 and a connector 224.

The blood manifold 22 is formed with a plurality of fingers 64 which extend outward from the same side of the manifold 22. These fingers 64 are spatially separated from each other and have a generally rectangular shape. The fingers 64 are also dimensioned to snugly fit between the adjacently disposed pleats 48 of the bellows 14 between the two side-by-side hollow fiber rows 31 and 33. The preferred blood manifold 222 is in the form of a cylinder adjoining two series of openings 265 along its length, spaced about 120° apart, each pair of openings aligned with a given pleat and having tubing 267 fixed therein and extending into the pleat for blood delivery there. As stated, the manifold is fixed in its position by the urethane potting material 60.

The gas manifold 26 is generally rectangular and formed with two side-by-side hollow compartments, as seen at 68 and 70, partitioned by wall 72. When the manifold 26 is secured to the device 10, each of these compartments 68 and 70 is arranged over rows 31 and 33 respectively of fiber open ends. The manifold 26 includes ports, i.e. 2B, to allow a gas, usually oxygen-containing, to be directed into one of these compartments 68 or 70 to then enter the fibers 202 through the open ends, and travel around the bellows 14 through the fibers, and exit through another port, i.e. 30. The compartment 68 and 70, in combination with the individual fibers, define a plurality of separate gas flow pathways around the bellows 14. The gas manifold 26 is mounted to the housing 12 contiguous with the urethane potting material 60.

Figures 5A, 5B:
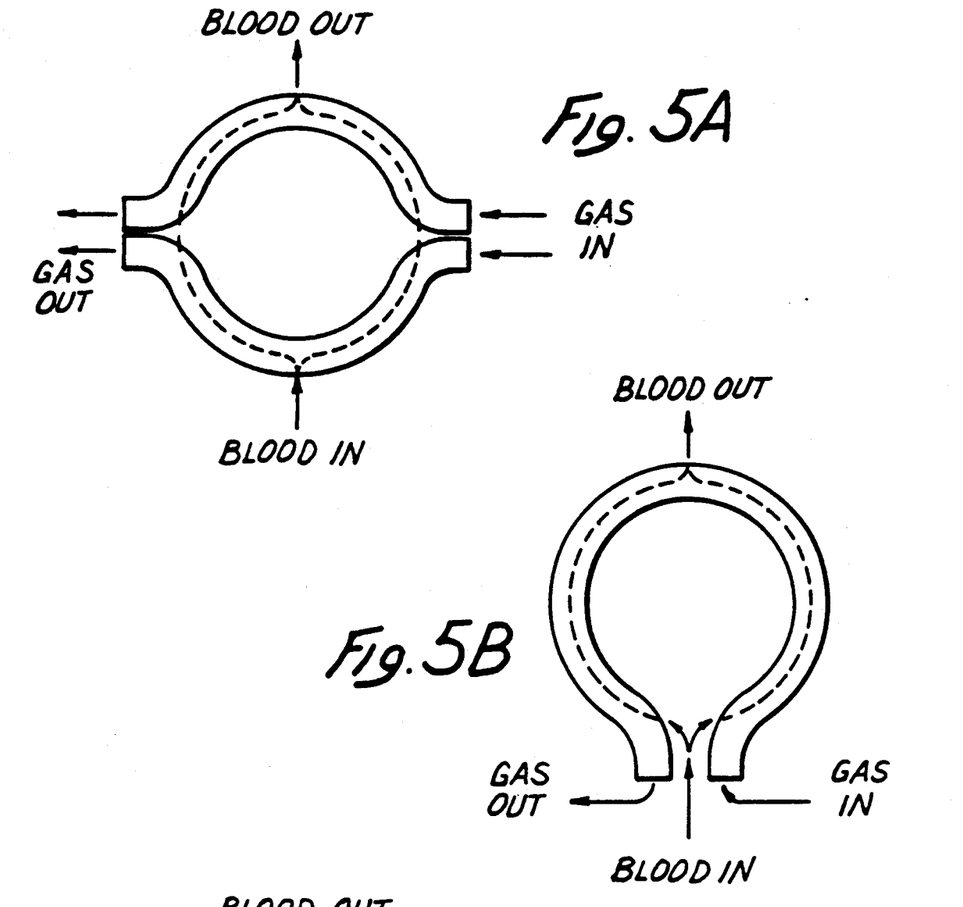
FIGS. 5A-C are schematic illustrations of different embodiments of a blood oxygenator/heat exchange devices in accordance with the invention illustrating the blood and gas flow paths through each such embodiment.
Figure 5C:
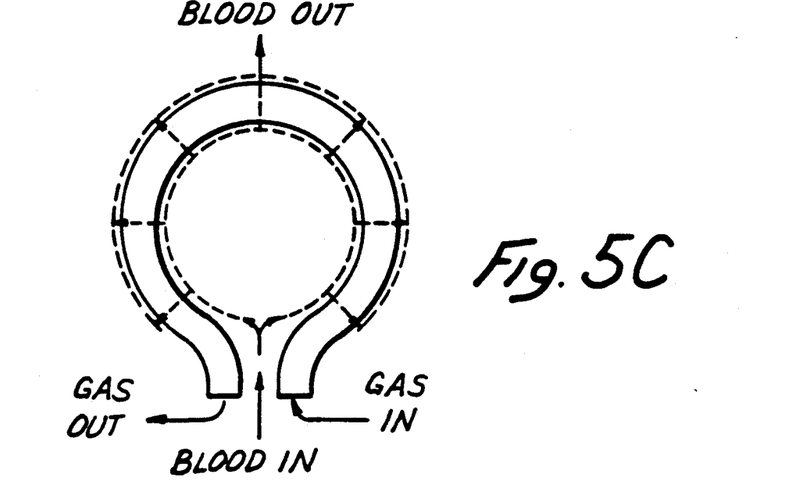

A more detailed description of the various components of the device 10 can be found in the parent case (which is fully incorporated herein by reference) specifically at pages 13 through 22 thereof, incorporated here. With brief reference to FIGS. 5A through 5C, other blood and gas flow paths with different outlet and inlet locations are shown and described in more detail in the parent application but the preferred embodiment is shown in the other figures.

While the heat exchange fluid pathway 38 is defined by the combination of the Jacket 16 or 216 nested in the bellows 14, the blood pathway is defined by the blood receiving channels 58, in combination with the gas exchange members defined by the woven ribbons 208. This is best shown in FIG. 11, although an alternate embodiment which shows the hollow fibers merely arranged in a bundle 32 rather than ribbons, is shown in FIG. 2A.

As illustrated in FIG. 11A, blood pathway 59 is essentially a gap between ribbons 208 and the base 210 of each pleat. In the preferred embodiment, hollow fiber woven ribbons 208 made as shown in FIGS. 9 and 10, sized to fit the channel, are laid down in pairs. Ribbons 208A contain 7 hollow fibers 202 and alternate with ribbons 208B, containing 6 hollow fibers 202. The number of fibers, of course, depends on the groove width, but the ribbons are preferably always laid down in alternating layers, with the hollow fibers of each layer for the most part offset with respect to those of adjacent layers to promote enhanced and uniform blood distribution.

Figure 11B:
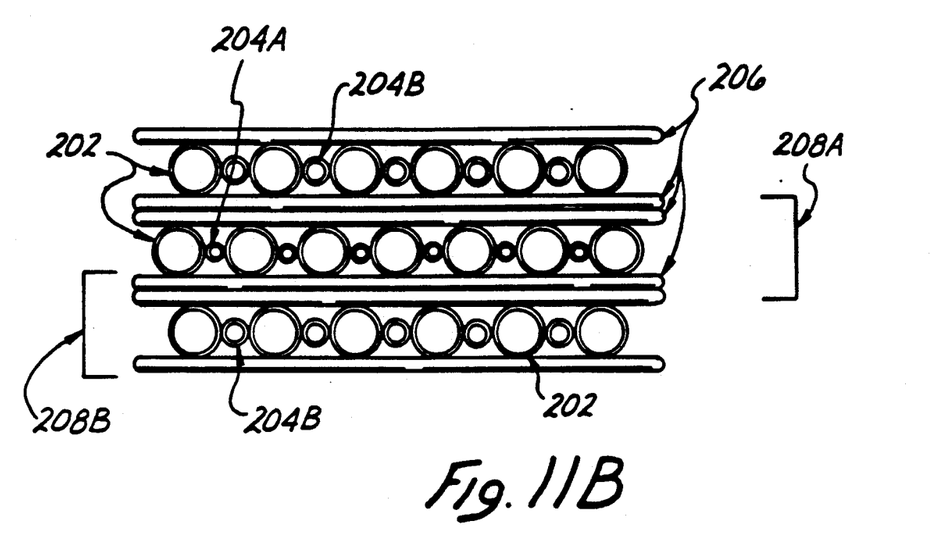
FIG. 11B is a schematic cross-section of three layers of ribbon of the preferred fluid treatment apparatus showing the relative spacing of the inert fibers and the hollow fibers which are layered in the blood flow channel.
Figure 11C:
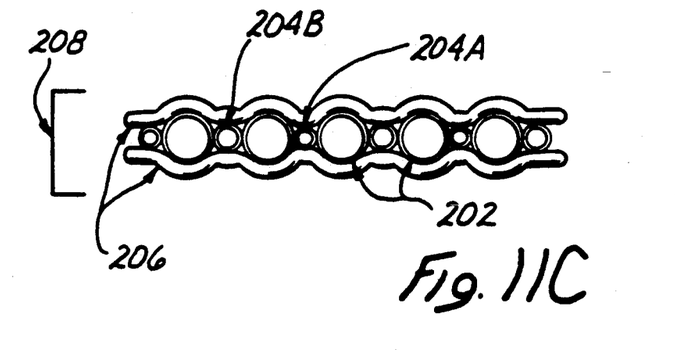
FIG. 11C is a schematic cross-section of a ribbon of the present invention showing an alternate spacing arrangement.

Most preferably, 7-fiber ribbon 208A contains first inert fibers 204A which have diameters about one-fifth the diameter of the hollow fiber, while 6-fiber ribbon 208B contains first inert fibers 204B having diameters about one-third the diameter of hollow fibers 202, as shown in FIG. 11B to render the hollow fibers of one layer largely offset from those of the adjacent layer. In the embodiment shown in FIG. 11B, the ribbons 208 are about ⅛ inch wide and the blood channel is about ¼ inch from side 49 to side 51, although of course pleats ranging from about 1/16 to about ½ inch or even more can be used. Alternately, layers of identical ribbons 208 having first inert fibers of alternating sizes as shown in FIG. 11C, can be used to obtain appropriate spacing.

A spacer 200 in the form of an inert plastic (usually polyester) coil of about one-eighth inch in diameter extends through the pleat in the blood channel 59 adjacent to pleat base 210 for the entire length of the pleat. It maintains the integrity of the blood passage 59 when ribbons 208A and 208B are wound through the pleat during manufacture of the oxygenator and thereafter.

It has been found that sufficient oxygenation is obtained when 32 layers of ribbon 208 are wound in each pleat, the voids about the fibers amounting to about 20 to 80, preferably 40 to 60 percent of the pleat, apart from passageway 59. Preferably 16 layers each of alternating ribbons 208A and 208B are wound in the pleat in pairs to form the 32 alternating, offset layers spaced from the base as shown in FIG. 11A. While the illustrated embodiment of the blood channel in pleat 58 shown in FIGS. 11 and 2A show a gap 59 between the base 210 and ribbons 208 or fiber bundle 32 to define the blood pathway 59, the ribbons 208 may in fact completely fill the individual channels 58. The resulting device 10 would not have blood pathways 59 as seen in the illustrated embodiment. That is, the pathways 59 would not be defined by a gap, but would merely be a pathway formed about the bellows 14 in the blood receiving channels 58 and between the hollow fibers 202.

Turning to the blood manifold 22 shown in FIG. 4, each finger 64 is formed with one or more open passages, one of which is seen generally at 66. Each of these passages 66 communicates with the conduit 62, and with the associated blood pathway 59 when the respective finger 64 is fitted between the pleats 48. Blood manifold 222, preferred, merely provides tubing 267 extending into each pleat. Blood entering the blood manifold 22 or 222 travels through the conduit 62 or 262, and selectively enters and flows through each of the passages 66 or 267. The blood will exit the passages 66 or 267 into the associated blood pathway 59, and travel through the individual blood pathway 59 about the bellows 14. As the gap defining the blood pathway 59 fills, the blood flows outward, about the hollow fibers 202 disposed in ribbons 208 in the associated blood receiving channel 58, and, once oxygenated, exits on the far side through exit 18.

As the blood flows about the individual hollow fibers 202, the exchange of gases occurs. This gas exchange is basically a diffusion process where the oxygen diffuses from the higher concentration in the gas across the fiber membrane to the blood, and the carbon dioxide diffuses from the higher concentration in the blood across the fiber membrane to the gas. The blood will thus become oxygenated as it passes around the individual hollow fibers, and will be subjected to heat exchange by direct contact with the thermally conductive surfaces 49 and 51 of the bellows 14.

The regulation of oxygen and carbon dioxide exchange can be independently controlled by regulating the flow rate of the oxygen-bearing gas through the hollow fibers 202, and by regulating the concentration of the oxygen in such gas. This manner of independently controlling the rate of oxygen and carbon dioxide exchange is known. However, it may be desirable to independently control the rate of carbon dioxide and oxygen exchange in a different manner. Accordingly, in accordance with another embodiment, the gas manifold 26 may be formed with each of the compartments 68 and 70 being further sub-divided into two or more separate portions by partition walls, with such walls being shown in phantom in FIG. 3 at 69 and 71. Preferably only that compartment functioning as the gas intake compartment is sub-divided in this manner. That is, only compartment 68 is subdivided into two separate portions. The remaining compartment 70 remains undivided. By introducing an oxygen-bearing gas into only one of the portions of compartment 68, while introducing an inert gas into the other portion, the level of carbon dioxide removal is maintained while the level of oxygen exchange is reduced. This is performed without adjusting the flow rate of the oxygen-bearing gas.

This desire to independently adjust the exchange rates for oxygen and carbon dioxide is particularly advantageous when the patient is under hypothermia, that is when the patient's blood temperature has been lowered. In this state the patient's requirement for oxygen diminishes since the patient's metabolism decreases. Thus the oxygenation requirement diminishes. However, the necessity of removing the carbon dioxide remains constant. The described embodiment of the device of the invention would allow for control in the level of oxygenation by merely fluctuating the delivery of the oxygen-bearing gas and the inert gas to the individual portions of the compartment 68.

Figure 6:
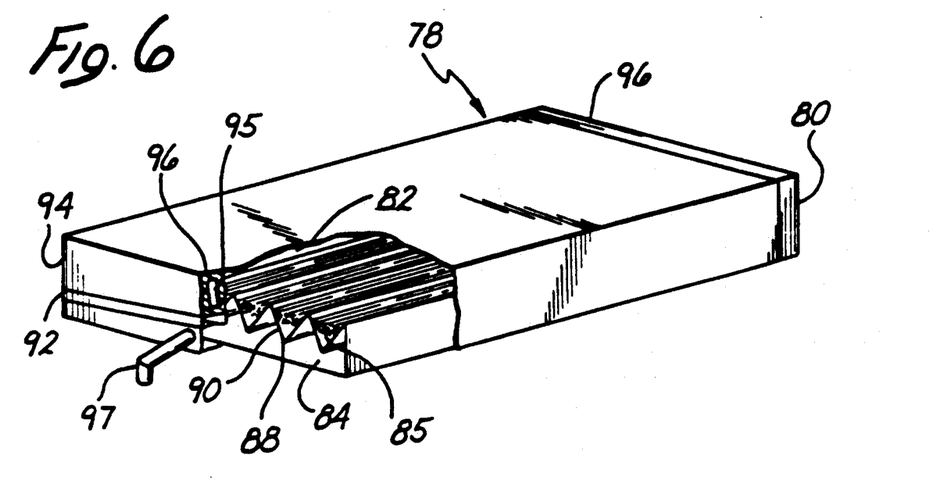
FIG. 6 is a partially sectioned prospective view of a blood oxygenator/heat exchange device is accordance with another embodiment of the invention.
Figure 7:
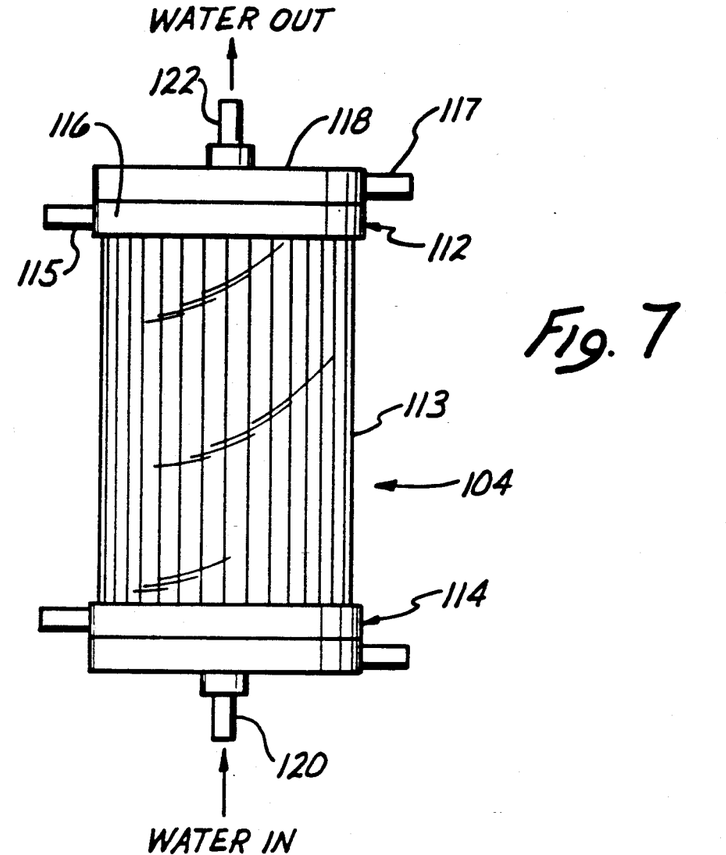
FIG. 7 is a side view of a blood oxygenator/heat exchange device is accordance with a further embodiment of the invention.
Figure 8:
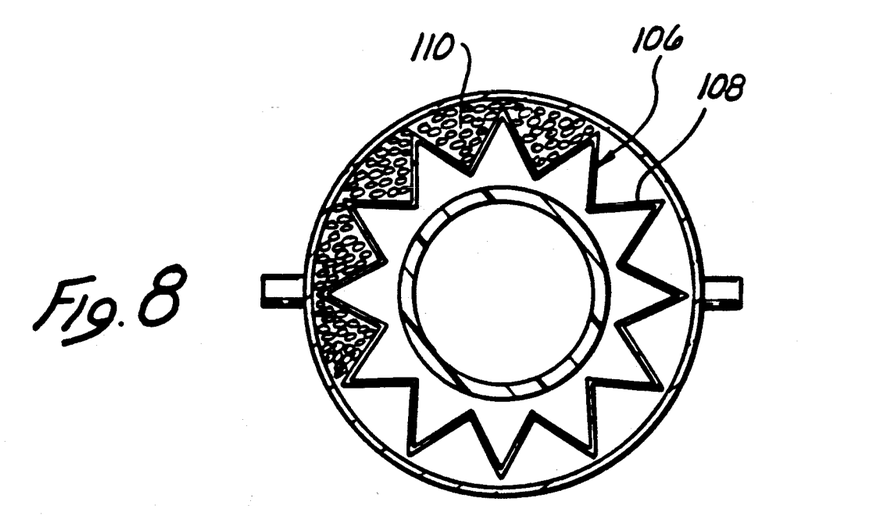
FIG. 8 is a cross-sectional view of the embodiment of the invention shown in FIG. 7.

Finally, alternate embodiments of the oxygenator are shown in FIGS. 6, 7 and 8. These are described in detail in the parent application, and can be used in conjunction with the hollow fiber membrane apparatus of the present invention as well, where the hollow fibers 202 are similarly, and preferably, laid down in alternating pairs of ribbons 208A and 208B in the pleats.

It should be noted here that the arrangement of woven ribbons which is described in the preferred embodiment has been found to be extremely effective in oxygen transfer. One of the better high efficiency oxygenators now available on the market contains non-woven microporous fiber believed to be laid down in the winding process described by U.S. Pat. No. 4,472,446, and referred to earlier. This winding process produces a fiber pattern in the above-mentioned commercial oxygenator found to have oxygen transfer efficiencies of about 150 mls $O_2$/minute per square meter of microporous fiber surface area; such an oxygen transfer rate is typical of other high efficiency oxygenators on the market. The woven hollow fiber arrangement described above, however, has been found to produce oxygenators with efficiencies even better than 200 mls $O_2$/minute per square meter of microporous fiber surface area. Furthermore, in the oxygenator described herein, the priming volume has been reduced to 225 mls of blood as opposed to 325 mls for the above-mentioned commercially available oxygenator.

While the preferred embodiments have been described and illustrated, various modifications and substitutions may be made thereto without departing from the scope of the invention. Accordingly, it is to be understood that the invention has been described by way of illustration and not limitation.

What is claimed is:

1. A hollow fiber membrane fluid treatment apparatus for the transfer of mass or energy through a membrane comprising:

a housing having first fluid inlet and outlet means and second fluid inlet and outlet means;

hollow fiber membranes extending substantially longitudinally within said housing, each hollow fiber membrane having a first end in fluid communication with the first fluid inlet means and a second end in fluid communication with the first fluid outlet means for flow of a first fluid therethrough, the second fluid inlet means arranged to flow a second fluid longitudinally along exteriors of the hollow fiber membranes and to the second fluid outlet means;

first inert fibers spaced between adjacent ones of the hollow fiber membranes, extending substantially longitudinally and substantially parallel with the hollow fiber membranes and comprising a warp consisting of alternating first inert fibers and hollow fiber membranes; and second inert fibers extending generally transverse to and contiguous with the hollow fiber membranes and the first inert fibers, every other second inert fiber passing over the hollow fiber membranes and under the first inert fibers and the remaining second inert fibers passing under the hollow fiber membranes and over the first inert fibers in an alternating pattern comprising a weft with the hollow fiber membranes and the first inert fibers to form a hollow fiber membrane weave.

2. A hollow fiber membrane fluid treatment apparatus according to claim 1 and wherein the hollow fiber membranes extend through the weave aligned straight relative to the first inert fibers.

3. A hollow fiber membrane fluid treatment apparatus according to claim 1 and wherein the first inert fibers are each about one tenth to one third the diameter of the hollow fiber membranes.

4. A hollow fiber membrane fluid treatment apparatus according to claim 3 and wherein the second inert fibers are each about one twentieth to one fifth the diameter of the hollow fiber membranes and spaced about five to the inch.

5. A hollow fiber membrane fluid treatment apparatus according to claim 4 wherein a plurality of layers of the weave are provided.

6. A hollow fiber membrane fluid treatment apparatus according to claim 7 wherein the hollow fiber membranes of each layer are generally offset with respect to those of an adjacent layer to promote fluid flow around the hollow fiber membranes.

7. A hollow fiber membrane fluid treatment apparatus according to claim 5 and wherein first layers in which the first inert fibers are about one-fifth the diameter of the hollow fiber membranes alternate with second layers in which the first inert fibers are about one-third the diameter of the hollow fiber membranes to promote even and uniform fluid flow around the hollow fiber membranes.

8. A hollow fiber membrane fluid treatment apparatus according to claim 7 and consisting essentially of multiple layers of the weave, the first layers each in the form of a ribbon containing a given number of hollow fiber membranes and the second layers each in the form of a ribbon containing a lesser number of hollow fiber membranes designed so that the hollow fiber membranes are offset form each other in alternate layers.

9. A hollow fiber membrane fluid treatment apparatus according to claim 1 and wherein the hollow fiber membranes are composed of a hydrophobic, biocompatible polymer material permeable to mass or energy to be transferred through the hollow fiber membrane, but resistant to the flow of fluid through the hollow fiber membrane.

10. A hollow fiber membrane fluid treatment apparatus according to claim 9 an wherein the first inert fibers are composed of a biocompatible monofilament selected to be flexible relative to the hollow fiber membranes, to promote precise spacing of the hollow fiber membranes.

11. A hollow fiber membrane fluid treatment apparatus according to claim 10 and wherein the second inert fibers are composed of a monofilament material selected from the group consisting of nylon, polyester, and polypropylene, to promote close controlled spacing between the hollow fiber membranes for largely even, uniform fluid flow over the hollow fiber membranes.

12. A hollow fiber membrane fluid treatment apparatus according to claim 1 wherein the first inert fibers extend along the longitudinal axis of the hollow fiber membranes in a sinusoidal fashion and the second inert fibers are woven between the sinusoidal peaks and troughs of the first inert fibers.

13. A woven hollow fiber membrane fluid treatment apparatus disposed within a housing for the transfer of mass or energy through a membrane comprising:
  hollow fiber membranes of a biocompatible material extending substantially longitudinally within the housing;
  first inlet and outlet means communicating with opposing ends of the hollow fiber membranes for directing a first fluid therethrough;
  conduit means disposed within the housing and having second inlet and outlet means in fluid communication with the hollow fiber membranes for directing a second fluid over exteriors of the hollow fiber membranes generally transverse to the hollow fiber membranes;
  first inert fibers of a biocompatible monofilament spaced between adjacent ones of said hollow fiber membranes so that the first inert fibers and the hollow fiber membranes form a warp consisting of alternating hollow fiber membranes and first inert fibers, the first inert fibers positioned substantially parallel to the orientation of the hollow fiber membranes; and
  second inert fibers of a biocompatible monofilament extending generally transverse to and contiguous with the hollow fiber membranes, and the fist inert fibers every other second inert fiber passing over the hollow fiber membranes and under the first inert fibers and the remaining second inert fibers passing under the hollow fiber membranes and over the first inert fibers in an alternating pattern to form a weft with the hollow fiber membranes and the first inert fibers.

14. A woven hollow fiber membrane fluid treatment apparatus according to claim 13 and wherein the hollow fiber membranes are formed in layers, the hollow fiber membranes of each layer generally offset with respect to the hollow fiber membranes of an adjacent layer to promote even fluid flow through the apparatus.

15. A woven hollow fiber membrane fluid treatment apparatus according to claim 14 and wherein the second fluid is a liquid, alternate layers contain first inert fibers about one-fifth the diameter of the hollow fiber membranes, and the remaining layers contain first inert fibers about one-third the diameter of the hollow fiber membranes to space the hollow fiber membranes in the apparatus to promote flow of the second fluid throughout.

16. A woven hollow fiber membrane fluid treatment apparatus according to claim 15 and wherein the hollow fiber membranes are formed of microporous polypropylene, the first inert fibers are formed of polyester, and the alternating layers contain either about six or about seven hollow fiber membranes per layer.

17. A woven hollow fiber membrane fluid treatment apparatus according to claim 14 and wherein the first inert fibers in each layer vary in size to very the spacing between the hollow fiber membranes.

18. A membrane oxygenator comprising apparatus for the transfer of oxygen to the blood, said apparatus having a blood inlet and outlet and a gas inlet and outlet and defining at least one channel having a base and forming a first conduit for the flow of blood from the blood inlet to the blood outlet, the at least one channel containing:
  hollow fiber membranes formed of a biocompatible material extending substantially lengthwise through the at least one channel to form a second conduit for gas flow, each hollow fiber membrane having a first end in fluid communication with the gas inlet and a second end in fluid communication with the gas outlet for flowing gases therethrough, the blood inlet arranged to flow blood longitudinally along exteriors of the hollow fiber membranes and the at least one channel to the blood outlet;
  first inert fibers spaced between adjacent one of the hollow fiber membranes and extending substantially parallel to the hollow fiber membranes, the hollow fiber membranes and the first inert fibers comprising a warp consisting of alternating first inert fibers and hollow fiber membranes; and
  second inert fibers extending transversely to and contiguously with the hollow fiber membranes and the fist inert fibers, every other second inert fiber passing over the hollow fiber membranes and under the first inert fibers and the remaining second inert fibers passing under the hollow fiber membranes and over the first inert fibers in an alternating pattern to form a weft with the hollow fiber membranes and the first inert fibers.

19. A membrane oxygenator according to claim 18 and wherein the first inert fibers and the second inert fibers are formed of a biocompatible material.

20. A membrane oxygenator according to claim 19 and wherein the first inert fibers are comprised of monofilament to promote precise spacing of the hollow fiber membranes and uniform flow of blood over them.

21. A membrane oxygenator according to claim 20 and wherein the first inert fibers are of alternating sizes to vary the spacing between hollow fiber membranes.

22. A membrane oxygenator according to claim 20 and wherein the first inert fibers are each about one fifth to one third the diameter of the hollow fiber membranes and the second inert fibers are each about one eighth to one fifth the diameter of the hollow fiber membranes, and spaced about five to the inch to promote the flow of thin films of blood and high oxygen transfer rates.

23. A membrane oxygenator according to claim 22 and wherein the hollow fiber membranes are disposed in the at least one channel in woven ribbons arranged in alternating layers, the first inert fibers in alternate layers being about one third the diameter of the hollow fiber membranes, and the first inert fibers in the remaining layers being about one fifth the diameter of the hollow fiber membranes so that the hollow fiber membranes in adjacent layers are generally offset from each other to promote even spacing between the layers and even blood-flow throughout.

24. A membrane oxygenator according to claim 22 and wherein woven ribbons are disposed in the at least one channel spaced from the base to define a gap therein.

25. A membrane oxygenator according to claim 24 and wherein the hollow fiber membranes are disposed in the at least one channel in about thirty-two woven ribbons having either about 6 or about 7 hollow fiber membranes each, and a coiled spacer extends the length of the at least one channel in the gap to maintain the integrity of the gap and the position of the ribbons during manufacture and use of the oxygenator.

26. A membrane oxygenator according to claim 20 and wherein the hollow fiber membranes are composed of microporous polypropylene, and both inert fibers are composed of polyester monofilament for precise and even spacing of the hollow fiber membranes and thin, uniform blood flow therethrough to promote high oxygen transfer rates with minimized blood injury.

27. A blood oxygenator and heat exchange device comprising:
   body means for defining a plurality of pathways through which blood can be passed, with each of the pathways comprising opposing ends and having disposed therein a hollow fiber membrane fluid transfer apparatus and means for defining a heat exchange surface;
   each of the fluid transfer apparatus comprising:
   hollow fiber membranes of a biocompatible material extending substantially longitudinally within the pathways;
   first inlet and outlet means disposed at opposing ends of the pathways and communicating with opposing ends of the hollow fiber membranes for directing a first fluid therethrough;
   conduit means disposed within the pathways and having second inlet and outlet means for directing a second fluid over exteriors of the hollow fiber membranes generally transverse to the hollow fiber membranes;
   first inert fibers of a biocompatible monofilament spaced between adjacent ones of said hollow fiber membranes so that the first inert fibers and the hollow fiber membranes form a warp consisting of alternating hollow fiber membranes and first inert fibers, the first inert fibers positioned substantially parallel to the orientation of the hollow fiber membranes; and
   second inert fibers of a biocompatible monofilament extending generally transverse to and contiguous with the hollow fiber membranes, and the first inert fibers, every other second inert fiber passing over the hollow fiber membranes and under the the first inert fibers and the remaining second inert fibers passing under the hollow fiber membranes and over the first inert fibers in an alternating pattern to form a weft with the hollow fiber membranes and the first inert fibers.

28. The blood oxygenator and heat exchange device of claim 27, wherein the conduit means consists of a housing formed to allow blood to pass therethrough and wherein the device further comprises heat and gas exchange means positioned in the housing for selectively exchanging heat and gas with blood passing through the housing, the heat and gas exchange means being formed with a plurality of blood flow pathways, each pathway having at least a first thermally conductive wall and one of the hollow fiber membrane fluid transfer apparatus; and
   wherein the hollow fiber membranes of each fluid transfer apparatus are formed in layers, the hollow fiber membranes of each layer generally offset with resect to the hollow fiber membranes of an adjacent layer to promote even fluid flow through the apparatus.

29. The blood oxygenator and heat exchange device of claim 28 wherein each of the hollow fiber membranes has an internal portion which defines a passage through which may be directed an oxygen bearing gas, each of the at least a first thermally conductive all formed to define a channel through which blood can pass, and a hollow fiber membrane fluid transfer apparatus is positioned in each channel.

30. The blood oxygenator and heat exchange device of claim 28, wherein the housing defines at least a first internal chamber and further comprises;
   at least a first thermally conductive core positioned inside the at least a first housing internal chamber, the at least a first core being formed with an internal region through which a heat exchange fluid can be directed, the at least a first core further being formed with at least a first external surface, the at least a first external surface being formed with a plurality of separate, adjacently positioned parallel blood receiving channels;
   wherein a hollow fiber membrane fluid transfer apparatus is arranged in each of the channels, each hollow fiber membrane defining a separate gas flow pathway which is open at opposite ends of the hollow fiber membranes;
   at least a first gas manifold associated with the housing which is formed with at least two gas channels, each of the at least two gas channels being formed to communicate with selective ends of the hollow fiber membranes, the at least two gas channels further being formed to communicate with ports through which gas can be selectively introduced or removed from the at least two gas channels; and
   at least a first blood manifold means mounted in the housing and adjacent to the at least a first core for delivering blood to the blood receiving channels.

31. The blood oxygenator and heat exchange device of claim 30 wherein the second fluid is a liquid, alternate layers contain first inert fibers about one-fifth the diameter of the hollow fiber membranes, and the remaining layers contain first inert fibers about one-third the diameter of the hollow fiber membranes to space the hollow fiber membranes in the apparatus to promote flow of the second fluid throughout.

32. The blood oxygenator and heat exchange device of claim 31 wherein the hollow fiber membranes are formed of microporous polypropylene, the first inert fibers are formed of polyester, and the alternating layers contain either about six or about seven hollow fiber membranes per layer.

* * * * *